United States Patent [19]

Viola

[11] Patent Number: 4,702,109

[45] Date of Patent: Oct. 27, 1987

[54] IN-LINE HYDROMETER

[75] Inventor: Frank J. Viola, Uniondale, N.Y.

[73] Assignee: Parker Hannifin Corporation, Cleveland, Ohio

[21] Appl. No.: 854,270

[22] Filed: Apr. 21, 1986

[51] Int. Cl.[4] .............................................. G01N 9/10
[52] U.S. Cl. ..................................................... 73/440
[58] Field of Search ................ 73/440, 444, 445, 311, 73/327, 319, 448; 116/228

[56] References Cited

U.S. PATENT DOCUMENTS 1,340,269  5/1920  Ivey et al. ............................. 73/440
2,631,182  3/1953  Hall et al. ............................ 116/228
3,631,727  1/1972  White ................................... 73/440
4,126,044  11/1978  Tichy et al. .......................... 73/440
4,237,096  12/1980  Popoff et al. ........................ 73/440

Primary Examiner—John Chapman
Attorney, Agent, or Firm—Christopher H. Morgan

[57] ABSTRACT

A hydrometer that measures the specific gravity of fluid in channels (36) of a hydrometer body (10). The specific gravity is determined according to the buoyancy of balls (40) that are located in each channel. Lenses (42) are provided in body (10) to aid in observing the position of balls (40). Pedestals (38) are provided in each channel to maintain balls (40) out of sediment accumulated at the bottom of the channels.

8 Claims, 3 Drawing Figures

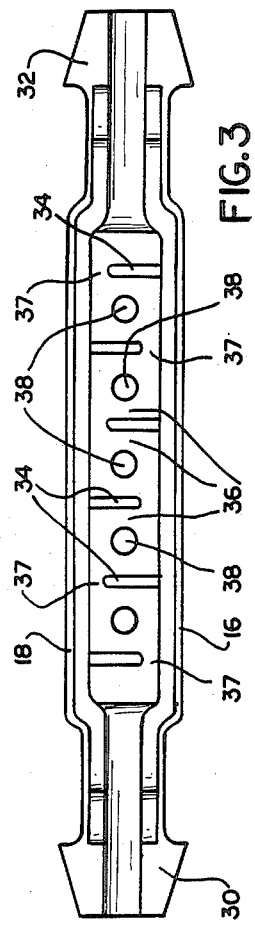
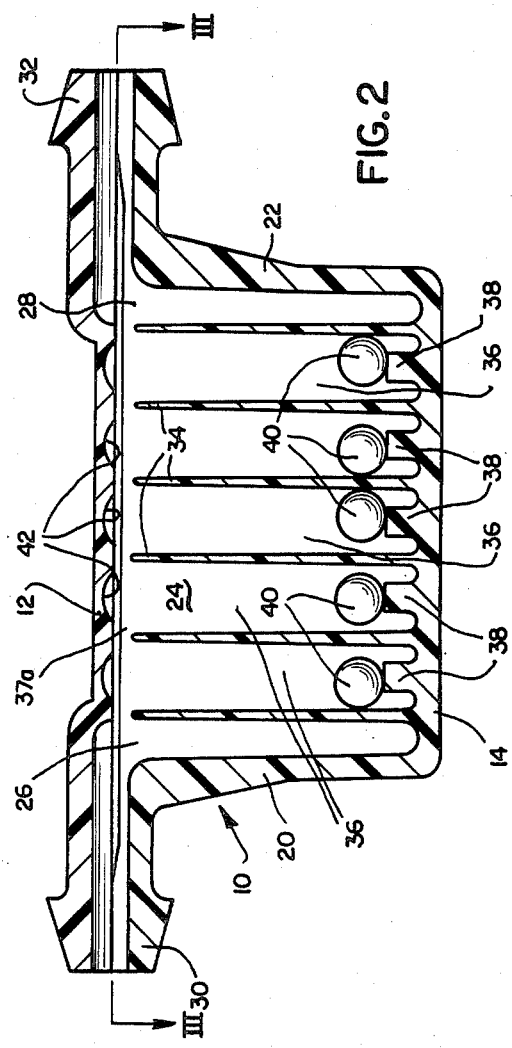
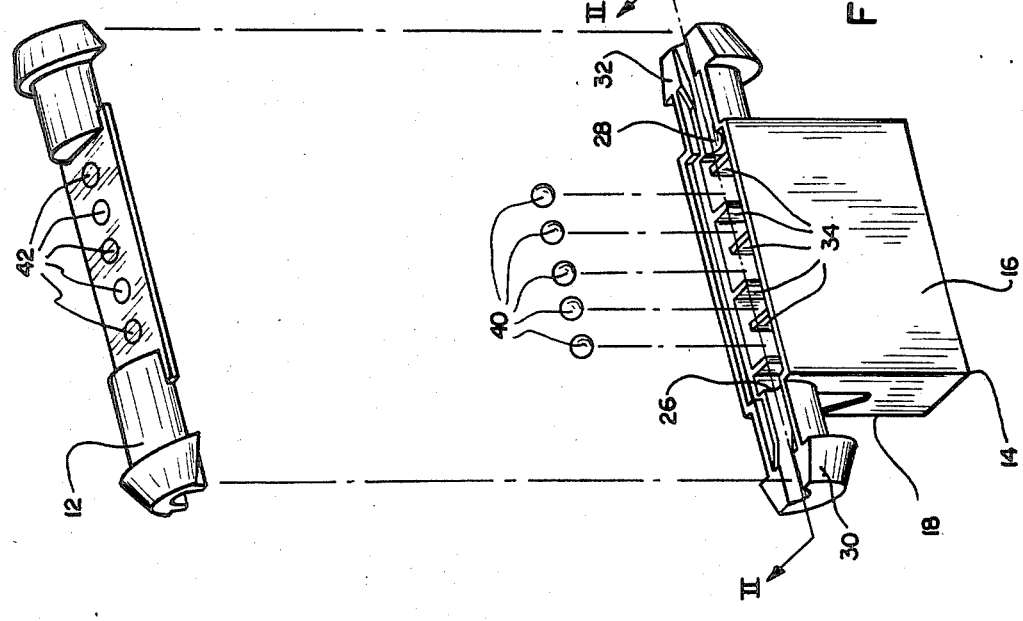

IN-LINE HYDROMETER

BACKGROUND OF THE INVENTION

1. Field of the Invention

The subject invention generally relates to hydrometers and, more specifically, hydrometers suited for continuous use in automotive applications.

2. Description of the Prior Art

Hydrometers have been used for many years to test the freezing points of coolant liquids in motor vehicles. Typically, these hydrometers have utilized float tubes with appropriate internal scales that provide a reading of the freezing point based upon the specific gravity of the coolant fluid. Examples are described in U.S. Pat. Nos. 1,578,193; 1,817,676; 1,890,900; and 2,002,183. Such hydrometers provide an accurate reading, but are relatively delicate and costly to construct and maintain.

Ball-type hydrometers have been developed for medical and other applications which are less precise, but more durable and less expensive. These hydrometers use balls of different specific gravity to continuously measure the specific gravity of the fluid. When a ball of a known specific gravity floats at the surface of the liquid, it is known that the specific gravity of the fluid is greater than the ball. By identifying which balls float on the surface of the liquid, the specific gravity of the liquid can be identified within a given range. Examples are shown in U.S. Pat. Nos. 1,556,185; 3,626,763; and 3,631,727.

In some of these systems, such as shown in U.S. Pat. No. 3,631,727, the balls are maintained in separate compartments to aid in identifying which balls are floating. However, such hydrometers were generally not well-suited for use in motor vehicles. The coolant fluids in motor vehicles generally contain relatively high quantities of impurities, because motor vehicle coolant systems are generally exposed to high levels of rust and dirt.

Accordingly, there was a need in the prior art for a simple, inexpensive hydrometer that was adapted for use on motor vehicles and that would quickly and reliably monitor specific gravity of a coolant fluid.

SUMMARY OF THE INVENTION

In accordance with the subject invention, a hydrometer includes a body that has an internal cavity and openings that provide communication of fluid to and from said cavity. The internal cavity of the body is separated into channels by several dividers and one of a plurality of balls is located in each channel. Each of the balls has a different specific gravity and each channel also includes a pedestal that is arranged to maintain the respective balls off of the bottom of the channel. Also, in accordance with the subject invention, a plurality of lenses are respectively located adjacent each channel and are arranged to magnify the balls when they are located adjacent the lenses.

Preferably, the lenses are located in a top member of the body and the pedestals are connected to a bottom member of the body with sidewalls extending between the top and bottom members.

Also preferably, passageways are provided between the divider and the surface of the internal cavity of the body such that the passageways establish communication between adjacent channels. Most preferably, a chamber is located adjacent the top member of the body. In this case, the dividers are fastened to the bottom member of the body.

Other details, objects and advantages of the subject invention will become apparent as the following description of a presently preferred embodiment proceeds.

BRIEF DESCRIPTION OF THE DRAWINGS

The accompanying drawings show a presently preferred embodiment of the invention in which:

FIG. 1 is an orthographic view of the preferred embodiment of an in-line hydrometer in accordance with the subject invention;

FIG. 2 is a cross-sectional view of the in-line hydrometer shown in FIG. 1 taken along the lines II—II; and FIG. 3 is a plane cross-section of the in-line hydrometer shown in FIGS. 1 and 2 and taken along the lines III—III of FIG. 2.

DESCRIPTION OF THE PREFERRED EMBODIMENT

As shown in FIGS. 1-3, the presently preferred embodiment of the subject invention is an in-line hydrometer for use in motor vehicle systems. The hydrometer includes a body 10 having a rectangularly-shaped top member 12 and a rectangularly-shaped bottom member 14 that is oppositely disposed apart from top member 12. Body 10 also includes two pairs of oppositely disposed sidewalls 16, 18 and 20,22 that extend between top member 12 and bottom member 14. The sidewalls 16, 18, 20 and 22 cooperate with top member 12 and bottom member 14 to define an internal cavity 24.

Sidewalls 16, 18 are provided with openings 26, 28 respectively. Openings 26, 28 communicate between internal cavity 24 and the outside of body 10 to permit flow of fluid through internal cavity 24. In the preferred embodiment, openings 26, 28 are provided through tubes 30 and 32. Tubes 30 and 32 provide convenient connection points for connecting body 10 to fluid lines in an automotive coolant system.

The preferred embodiment of the hydrometer further includes a plurality of dividers 34 that are secured to bottom member 14 and one of sidewalls 16 or 18. Dividers 34 extend into internal cavity 24. Dividers 34 cooperate with sidewalls 16 and 18 to define a plurality of channels 36 between adjacent dividers 34 and between dividers 34 and sidewalls 20 and 22. As shown in FIGS. 1-3, dividers 34 are tapered such that the cross-sectional area decreases in the direction away from base member 14 and toward top member 12. Accordingly, channels 36 are conversely tapered such that they increase in cross-sectional area in the direction away from bottom member 14. Dividers 34 cooperate with the internal surface of sidewalls 16 and 18 to further define passageways 37 such that adjacent channels 36 communicate through passageways 37. In addition, dividers 34 cooperate with top member 12 to define a chamber 37a that is common to all channels 36.

A plurality of pedestals 38 are respectively located in channels 36 and are secured to bottom member 14. A plurality of balls 40 are also respectively located in channels 36. Balls 40 are of different specific gravities but have substantially the same diameter. Balls 40 are sized such that, when no liquid is present in channels 36, they move freely between the top of the respective pedestals 38 and the inner surface of top member 12. However, balls 40 are large enough that they do not travel past dividers 34 and remain in their respective channels 36.

In the preferred embodiment, balls 40 are arranged in between openings 26 and 28 in order of increasing specific gravity. Also in the preferred embodiment, balls 40 are color coded according to their specific gravity so that they can be easily identified.

A plurality of lenses 42 is fixed in top member 12 at a location corresponding to each of channels 36. Lenses 42 are concave-shaped such that when the balls are within the focal length of the lens the balls are magnified as viewed outside of top member 12. In the preferred embodiment, lenses 42 are molded as an integral part of the top member 12.

In the operation of the preferred embodiment, the in-line hydrometer is connected into an engine coolant system. Preferably, in an automobile, the in-line hydrometer is connected in the coolant recovery system by connecting tubes 30 and 32 to the line between the radiator filler neck and the coolant recovery reservoir. Connecting the hydrometer outside the pressurized portion of the cooling system in this manner permits the hydrometer body to be constructed of thin walled, lightweight, transparent, injection molded thermoplastic material. As engine coolant flows between the filler neck and the reservoir, it passes through openings 26 and 28 of body 10 and, thus, fills and ultimately flows through internal cavity 24.

Inside internal cavity 24, the coolant flows past dividers 34 and through channels 36 and chamber 37a. As the coolant is flowing through channels 36, balls 40 are either supported by the fluid against the lens 42 of their respective channel, or reside at the bottom of the channel 36 adjacent bottom member 14 where balls 40 are supported by the top surface of pedestals 38. The position of respective balls 40 depends upon the relative specific gravity of the balls 40 and the coolant.

Since lenses 42 magnify balls 40 when they are against the lenses, the buoyant condition of balls 40 can readily be observed. Thus, by observing which balls are maintained against lenses 42 and which are not, the specific gravity of the coolant can be identified within a known range. Once the specific gravity of the coolant is known, the ethylene glycol content is assumed and the freezing point of the coolant can readily be determined within a specific range of temperature. Since balls 40 are color coded, this calculation can be made with the aid of an appropriate nomograph or similar chart that is appropriately labeled.

Pedestals 38 are of particular advantage in the operation of the subject device in that they maintain balls 40 at a distance away from the inner surface of bottom member 14. Thus, balls 40 avoid being trapped in any sediment that may accumulate at the bottom of channels 36. This arrangement also tends to limit the deposition of sediment material on balls 40 which will alter the specific gravity of the balls and, thus, impact the accuracy of any readings that are taken.

While a presently preferred embodiment of the subject invention is shown and described herein, it is to be understood that the invention is not limited thereto but may be otherwise variously embodied within the scope of the following claims.

I claim:

1. An in-line hydrometer for connection in an engine coolant system between a radiator filler neck and an overflow reservoir, said hydrometer comprising:
    a body that includes an internal cavity having a bottom surface, said body further having first and second openings respectively located on opposite sides of said body, and that communicate between said internal cavity and the outer surface of said body;
    a plurality of dividers that extend into the cavity of said body and that cooperate with said body to define channels between adjacent dividers;
    a plurality of balls having different specific gravity, each of said balls being located in a respective one of said channels; and
    a plurality of pedestals, each of said pedestals being located in a respective one of said channels adjacent the bottom of said channel, said pedestals maintaining said balls apart from the bottom surface of said internal cavity.

2. The in-line hydrometer of claim 1 wherein the internal cavity of said body includes a top surface, said in-line hydrometer further comprising:
    a plurality of lenses that are located in said body adjacent said top surface, each of said lens corresponding to a respective one of said channels.

3. The in-line hydrometer of claims 1 or 2 wherein said first and second openings are respectively included in first and second tubes.

4. The in-line hydrometer of claims 1 or 2 wherein passageways are provided between said dividers and the surface of said internal cavity such that adjacent channels communicate with each other through said passageways.

5. The in-line hydrometer of claim 2 wherein openings are provided between said dividers and the top surface of said internal cavity with such openings combining to form a chamber in said internal cavity.

6. The in-line hydrometer of claims 1 or 2 wherein said body includes a top member and a bottom member with sidewalls extending between said top and bottom members.

7. The in-line hydrometer of claims 1 or 2 wherein said dividers are fastened to said bottom surface to secure said dividers in fixed position in the internal cavity of said body.

8. The in-line hydrometer of claim 2 wherein said body includes a top member and wherein said lenses are located in said top member with the inner surfaces of said lenses being concave such that when the balls are within the focal length of said concave surface, they are magnified by said concave surface.

* * * * *